(12) United States Patent
Yan

(10) Patent No.: US 9,831,433 B2
(45) Date of Patent: Nov. 28, 2017

(54) CONJUGATED POLYMERS AND DEVICES INCORPORATING THE SAME

(71) Applicant: Raynergy Tek Incorporation, Hsinchu (TW)

(72) Inventor: He Yan, Hong Kong (CN)

(73) Assignee: RAYNERGY TEK INCORPORATION, Hsinchu (TW)

(*) Notice: Subject to any disclaimer, the term of this patent is extended or adjusted under 35 U.S.C. 154(b) by 164 days.

(21) Appl. No.: 14/891,562

(22) PCT Filed: Dec. 26, 2014

(86) PCT No.: PCT/US2014/072437
§ 371 (c)(1),
(2) Date: Nov. 16, 2015

(87) PCT Pub. No.: WO2015/100441
PCT Pub. Date: Jul. 2, 2015

(65) Prior Publication Data
US 2016/0141499 A1   May 19, 2016

Related U.S. Application Data

(60) Provisional application No. 61/964,173, filed on Dec. 26, 2013.

(51) Int. Cl.
| | |
|---|---|
| C08F 30/04 | (2006.01) |
| H01B 1/00 | (2006.01) |
| H01L 31/00 | (2006.01) |
| H01L 51/00 | (2006.01) |
| C07D 417/14 | (2006.01) |
| C07D 421/14 | (2006.01) |
| C08G 61/12 | (2006.01) |

(Continued)

(52) U.S. Cl.
CPC ........ *H01L 51/0036* (2013.01); *C07D 417/14* (2013.01); *C07D 421/14* (2013.01); *C08G 61/123* (2013.01); *C08G 61/124* (2013.01); *C08G 61/126* (2013.01); *H01L 51/0043* (2013.01); *H01L 51/0047* (2013.01); *C08G 2261/1412* (2013.01); *C08G 2261/18* (2013.01); *C08G 2261/228* (2013.01); *C08G 2261/3223* (2013.01); *C08G 2261/3241* (2013.01); *C08G 2261/3246* (2013.01); *C08G 2261/51* (2013.01); *C08G 2261/91* (2013.01); *H01L 51/424* (2013.01); *H01L 51/5056* (2013.01); *Y02E 10/549* (2013.01); *Y02P 70/521* (2015.11)

(58) Field of Classification Search
CPC . C07D 421/14; C07D 417/14; H01L 51/0036; H01L 51/0047; H01L 51/0043; H01L 51/424; H01L 51/5056; C08G 61/126; C08G 61/124; C08G 61/123; C08G 2261/91; C08G 2261/51; C08G 2261/3246; C08G 2261/3241; C08G 2261/3223; C08G 2261/18; C08G 2261/1412; C08G 2261/228; Y02E 10/549; Y02P 70/521
USPC .......................... 526/240; 252/500; 136/263
See application file for complete search history.

(56) References Cited

U.S. PATENT DOCUMENTS

2013/0092912 A1* 4/2013 You .................... H01L 51/0036
257/40

* cited by examiner

*Primary Examiner* — William Cheung
(74) *Attorney, Agent, or Firm* — WPAT, PC

(57) ABSTRACT

Disclosed are conjugated polymers having desirable properties as semiconducting materials. Such polymers are cheap and easy to synthesize, and can exhibit good solubility and great solution processability, and that enable highly efficient OPVs.

23 Claims, 5 Drawing Sheets

Ar unit used in prior art benzodithiophene or BDT

Ar unit used in this invention bithiophene

(51) Int. Cl.
*H01L 51/42* (2006.01)
*H01L 51/50* (2006.01)

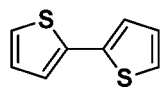
Ar unit used in prior art
benzodithiophene or BDT
Ar unit used in this invention
bithiophene
FIG. 1A
FIG. 1B
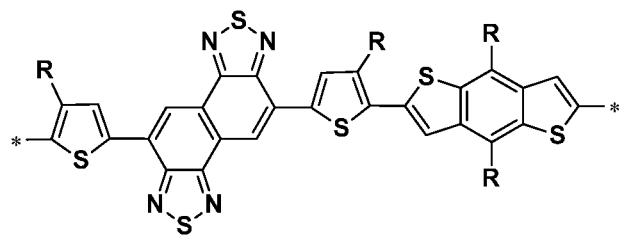
Prior art polymer with BDT unit
Achieved a high efficiency of 8.4%
FIG. 2A
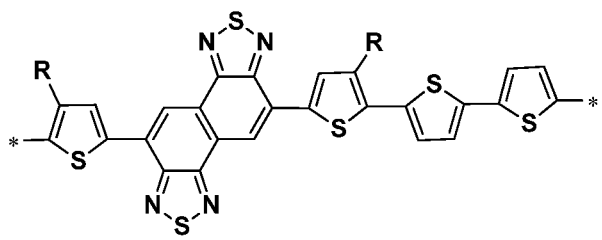
Prior art polymer with simple bithiophen unit
Only achieved a efficiency of 6.3%
FIG. 2B

2-decyltetradecyl, or 2DT, C10C14

2-octyldodecyl, or 2OD, C8C12

Prior art polymer with 2DT alkyl chain achieved 6.9% efficiency

Prior art polymer with 2OD alkyl chain achieved 1.6% efficiency

CONJUGATED POLYMERS AND DEVICES INCORPORATING THE SAME

CROSS REFERENCE TO RELATED APPLICATIONS

This application is a Section 371 National Stage Application of International Application No. PCT/US14/72437, filed on Dec. 26, 2016, which claims priority to and the benefit of U.S. Provisional Patent Application Ser. No. 61/964,173, filed on Dec. 26, 2013, the disclosure of which is incorporated by reference in its entirety.

BACKGROUND OF THE INVENTION

1. Field of the Invention

The present invention relates to novel conjugated polymers, methods for their preparation and intermediates used therein, mixtures and formulations containing them, the use of the compounds, mixtures and formulations as semiconductor in organic electronic (OE) devices, especially in organic photovoltaic (OPV) and organic field-effect transistor (OFET) devices, and to OE and OPV devices comprising these compounds, mixtures or formulations.

2. Description of the Prior Art

In recent years there has been growing interest in the use of organic semiconductors, including conjugated polymers, for various electronic applications.

One particular area of importance is the field of organic photovoltaics (OPV). Organic semiconductors (OSCs) have found use in OPV as they allow devices to be manufactured by solution-processing techniques such as spin casting and printing. Solution processing can be carried out cheaper and on a larger scale compared to the evaporative techniques used to make inorganic thin film devices. State-of-the-art OPV cells contain a blend film of a conjugated polymer and a fullerene derivative, which function as electron donor and electron acceptor, respectively. In order to achieve highly efficient OPVs, it is important to optimize both the polymer (donor) and fullerene (acceptor) components and to find a material combination yielding an optimal bulk heterojunction (BHJ) morphology that supports efficient exciton harvesting and charge transport properties. Recent improvements in the efficiencies of single junction OPVs (efficiency ~8-9%) have largely been due to the development of low-band-gap polymers, which are defined as polymers with an absorption onset at least 750 nm or more and with a band-gap of 1.65 eV or less.

A serious drawback of polymer and polymer/fullerene materials that have been suggested in prior art for use in OPV devices is that all high-efficiency OPVs have a relatively thin active layer (100-150 nm), which limits the light harvesting ability of the polymer/fullerene film and makes it challenging to apply such thin films to industry processes. When the thickness of the active layer is increased (e.g., to 300 nm), the fill factor (FF) of the cell typically suffers a dramatic decrease (below 60%), which results in poor efficiencies. The low FF and efficiency of thick polymer semiconductors (PSCs) are likely due to the limited charge transport ability of the polymer and impure polymer domains, among other factors. One way to achieve efficient thick-film PSCs is by obtaining morphologies that contain highly crystalline and pure polymer domains with excellent charge transport abilities. Obtaining a morphology with highly crystalline and pure, yet still reasonably small (e.g., 20 nm), polymer domains is a fundamental challenge.

SUMMARY OF THE INVENTION

In order to overcome the drawbacks of prior arts, the present invention provides various embodiments described below.

In one embodiment, a conjugated polymer containing 10 or more repeating units of Formula (I) is provided:

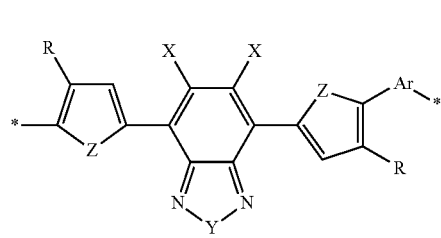

Formula (I)

wherein:
X, at each occurrence, independently is selected from F and Cl;
Y is selected from S or N—R1, wherein R1 is selected from C1-20 straight-chain or branched alkyl groups;
Z, at each occurrence, independently is selected from S and Se;
R, at each occurrence, independently is selected from straight-chain, branched or cyclic alkyl with 2-40 C atoms, in which one of more non-adjacent C atoms are optionally replaced by —O—, —S—, —C(O)—, —C(O—)—O—, —O—C(O)—, —O—C(O)—O—, —CR0=CR00— or —C≡C— and in which one or more H atoms are optionally replaced by F, Cl, Br, I or CN, or denote aryl, heteroaryl, aryloxy, heteroaryloxy, arylcarbonyl, heteroarylcarbonyl, arylcarbonyloxy, heteroarylcarbonyloxy, aryloxycarbonyl or heteroaryloxycarbonyl having 4 to 30 ring atoms that is unsubstituted or substituted by one or more non-aromatic groups; and
Ar is selected from unsubstituted or substituted arylene, or unsubstituted or substituted heteroarylene, or combination of such groups; Ar does not contain any polycyclic group.

In another embodiment, a conjugated polymer containing 10 or more repeating units of Formula (II) is provided:

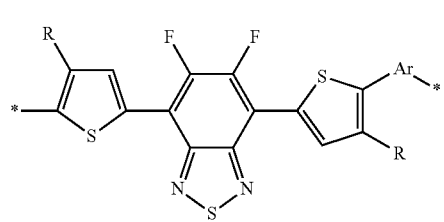

Formula (II)

wherein:
R, at each occurrence, independently is selected from straight-chain, branched or cyclic alkyl with 2-40 C atoms; and
Ar is selected from thiophene-based structure, or selenophene-based structure, or unsubstituted or substituted benzene-based structure, or combination of such groups; Ar does not contain any polycyclic group.

In still another embodiment, a conjugated polymer containing 10 or more repeating units of Formula (III) is provided:

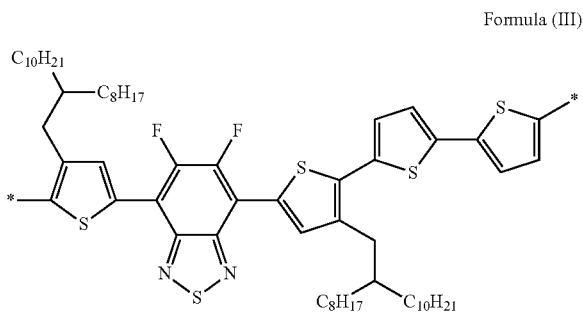

Formula (III)

wherein the number average molecular weight of the polymer is at least 30,000 gram/mole, or more preferably 40,000 gram/mole.

In one aspect, the present invention provides compounds for use as organic semiconducting materials that do not have the drawbacks of prior art materials as described above, are easy to synthesize, especially by methods suitable for mass production, and do especially show advantageous properties, especially for OPV and OTET use.

In another aspect, the present invention provides new conjugated polymers that would enable highly efficient thick-film (300 nm) OPVs, via the formation of a polymer/fullerene morphology containing highly crystalline, yet sufficiently small polymer domains.

In still another aspect, the present invention provides new conjugated polymers that are cheap and easy to synthesize, that exhibit good solubility and great solution processibility, and that enable highly efficient OPVs.

The above description is only an outline of the technical schemes of the present invention. Preferred embodiments of the present invention are provided below in conjunction with the attached drawings to enable one with ordinary skill in the art to better understand said and other objectives, features and advantages of the present invention and to make the present invention accordingly.

BRIEF DESCRIPTION OF THE DRAWINGS

The present invention can be more fully understood by reading the following detailed description of the preferred embodiments, with reference made to the accompanying drawings, wherein:

FIG. 1A shows the structure of a common Ar unit (BDT) in prior art. FIG. 1B shows one example structure of the Ar unit used in this invention FIG. 2A shows the structure of a prior art polymer based on BDT that exhibits 8.4% efficiency. FIG. 2B shows the results in prior art that replacing the BDT unit with bithiophene led to significantly reduced efficiency to 6.3%.

DETAILED DESCRIPTION OF THE PREFERRED EMBODIMENTS

Figure 3A:
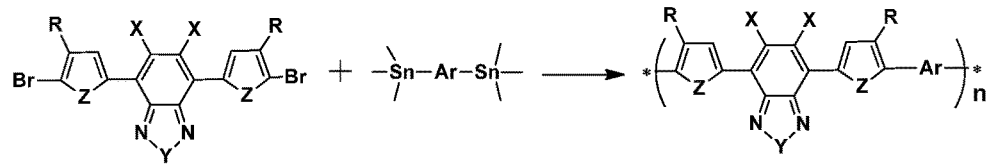
FIG. 3A shows the general synthetic route for polymers in present invention.

The present invention provides novel conjugated polymers, methods for their preparation and intermediates used therein, mixtures and formulations containing them, the use of the compounds, mixtures and formulations as semiconductor in organic electronic (OE) devices, especially in optical, electronic, or optoelectronic device comprising the conjugated polymer. The device is selected from an organic field-effect transistor (OFET), an organic light-emitting transistor, and an organic photovoltaic device (OPV). Additionally, the OE and OPV devices comprising these compounds, mixtures or formulations.

In the application, where an element or component is said to be included in and/or selected from a list of recited elements or components, it should be understood that the element or component can be one or more of the recited elements or components, or can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "contain", "contains", "containing", "include," "includes", "including," "have," "has," or "having" should be generally understood as open-ended and non-limiting unless specifically stated otherwise.

As used herein, "polycyclic groups" are molecules containing two or more rings fused together by sharing two neighboring atoms (i.e., sharing a common bond) and/or connected to each other via a spiro atom, or one or more bridged atoms, wherein at least one of the rings is aromatic, and at least one other ring that can be aromatic or non-aromatic, and carbocyclic or heterocyclic. A "polycyclic group" can include, for example, thieno[3,2-b]thiophene.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Throughout the specification, structures may or may not be presented with chemical names. Where any question arises as to nomenclature, the structure prevails.

In a first embodiment of the present invention, a conjugated polymer containing 10 or more repeating units of Formula (I) is provided:

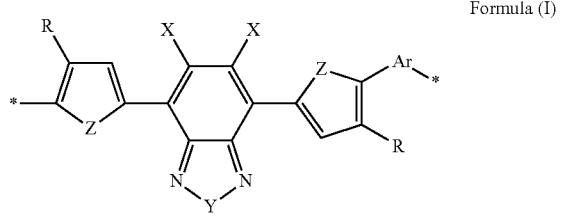

Formula (I)

wherein:
X, at each occurrence, independently is selected from F and Cl;
Y is selected from S or N—R1, wherein R1 is selected from C1-20 straight-chain or branched alkyl groups;
Z, at each occurrence, independently is selected from S and Se;
R, at each occurrence, independently is selected from straight-chain, branched or cyclic alkyl with 2-40 C atoms, in which one of more non-adjacent C atoms are optionally replaced by —O—, —S—, —C(O)—, —C(O—)—O—, —O—C(O)—, —O—C(O)—O—, —CR0=CR00- or —C≡C— and in which one or more H atoms are optionally replaced by F, Cl, Br, I or CN, or denote aryl, heteroaryl, aryloxy, heteroaryloxy, arylcarbonyl, heteroarylcarbonyl, arylcarbonyloxy, heteroarylcarbonyloxy, aryloxycarbonyl or heteroaryloxycarbonyl having 4 to 30 ring atoms that is unsubstituted or substituted by one or more non-aromatic groups; and
Ar is selected from unsubstituted or substituted arylene, or unsubstituted or substituted heteroarylene, or combination of such groups; Ar does not contain any polycyclic group. In one example of this embodiment, Ar is preferred oligo-thiophene or oligo-selenophene (such as bithiophen).

In one prior art, polymers based on a difluoro-2,1,3-benzothiadiazol (ffBT) and a fused benzodithiophene (BDT) aromatic comonomers unit having the following structure (PBnDT-DTffBT) have been proposed for use in OPV devices. However, PBnDT-DTffBT-based materials and devices were reported to still have limitations. For example, it was reported that the power conversion efficiency of OPV devices based upon a polymer/fullerene blend of a PBnDT-DTffBT polymer was limited to 7%. The large size of the BDT comonomer results in poor solubility and processibility of the OPV device. In addition, the BDT building block reported involves a quite lengthy synthetic route, which increases the cost of the material. The band-gap of PBnDT-DTffBT (1.7 eV) is also outside the optimal range for low-band-gap polymers.

Compared to the polymers of prior art in which a large fused aromatic ring (such as benzodithiophene, BDT, FIG. 1A) is used as the Ar unit, polymers of the present invention can use a simple bithiophene unit (FIG. 1B) as the Ar unit.

Replacement of BDT units with bithiophene unit led to unexpected improvements for example regarding the solubility and morphology profile, and results in surprising improvements regarding their OFET and OPV device performance. The majority of state-of-the-art low-band-gap polymers contain the BDT (FIG. 1A) unit and replacement of BDT with oligo-thiophene (such as bithiophene, FIG. 1B) lead to dramatically reduced OPV efficiency (from 8.4% to 5.6%) provided by two polymers of prior arts. In one prior art paper (*Energy Environ. Sci.,* 2012, 5, 8208), a polymer with BDT unit yielded OPV cells with 8.4% efficiency (FIG. 2A). In another prior art paper (*J. Am. Chem. Soc.* 2012, 134, 3498-3507), when the BDT unit is replaced with bi-thiophene unit, the best efficiency of the OPV cells is only 6.3% (FIG. 2B).

However, in this invention, the replacement of BDT with oligo-thiophene (such as bithiophene) or oligo-selenophene for the conjugated polymer has led to surprising and dramatic improvements of OPV efficiency from 7% to 10.8%, a new world record of single junction OPV to date.

In another example of this embodiment, the group Ar of the conjugated polymer, does not contain any alkyl substitution group, so as to obtain preferred polymer with higher molecular weight (for example, the number average molecular weight of the conjugated polymer is at least 30,000 gram/mole).

Figure 3B:
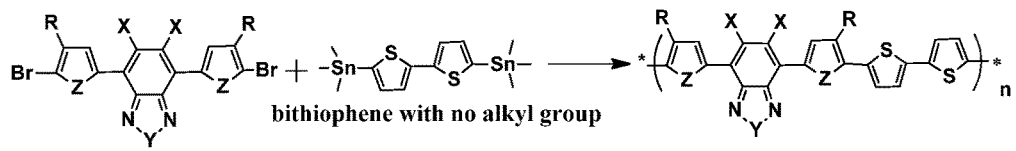
FIG. 3B shows one example of the synthesis of polymers in present invention with the Ar unit being bithiophene with no alkyl group.
Figure 3C:
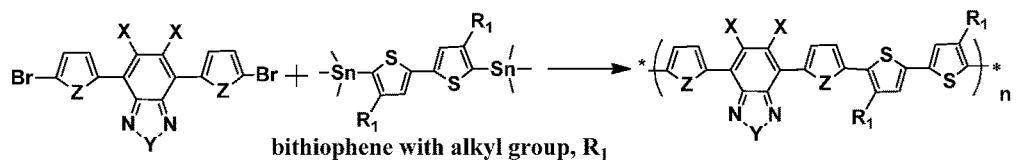
FIG. 3C shows a comparative example (with lower performance), in which the Ar unit is a bithiophene with alkyl group, $R_1$.
Figure 3D:
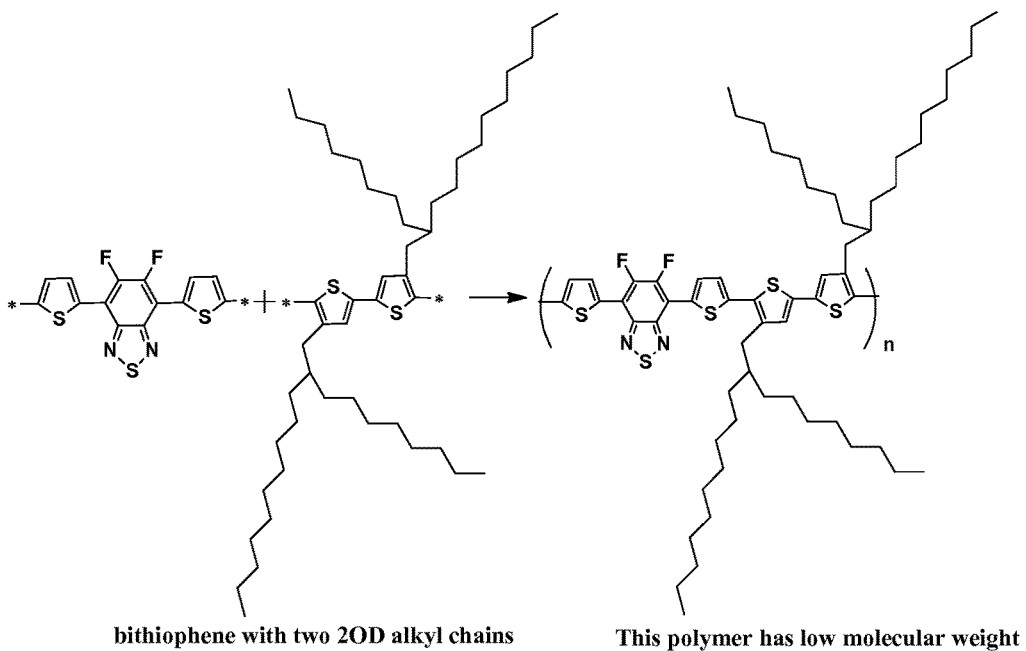
FIG. 3D shows a comparative example (with lower performance), in which the Ar unit is a bithiophene with 2OD alkyl chains.

Reasons are listed as follows, the conjugated polymer in the present invention are synthesized by reacting the distannyl reagent of the Ar unit with the dibromide of the other comonomer as shown in FIG. 3A. It is important that the Ar unit does not contain any alkyl substitution group such as the bithiophene unit shown in FIG. 3B. If the Ar unit contains alkyl groups (as shown in FIG. 3C), it would be challenging to obtain the distannyl reagent of the Ar unit (FIG. 3C). In addition, it was found that the Ar unit that contains two 2-octyldodecyl, or 2OD (C8C12) alkyl chains is difficult to synthesize and purify and the resulting polymer has low molecular weight and poor performance (FIG. 3D).

In still another example of this embodiment, the group R of the conjugated polymer, at each occurrence, independently is selected from branched alkyl groups with 15-25 carbon atoms, or with 17-23 carbon atoms, or more preferably 18-22 carbon atoms.

Figure 4A:
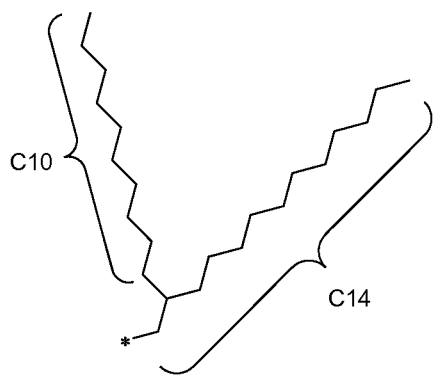
FIG. 4A and FIG. 4B show the structures of 2DT and 2OD alkyl chains.
Figure 4B:
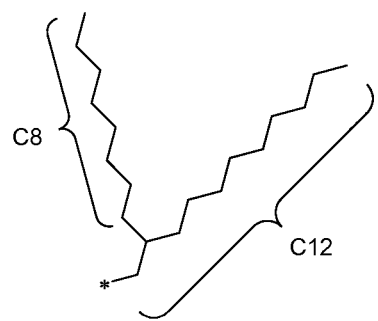
Figure 4C:
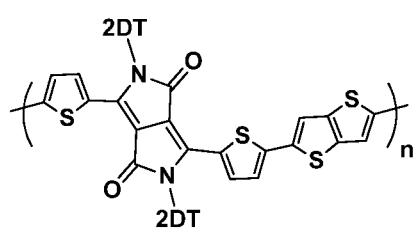
FIG. 4C and FIG. 4D show the structures of two prior art polymers with 2DT or 2OD alkyl chains. The polymer based on longer alkyl chain (2DT) exhibits much higher efficiency than that based on 2OD chain.
Figure 4D:
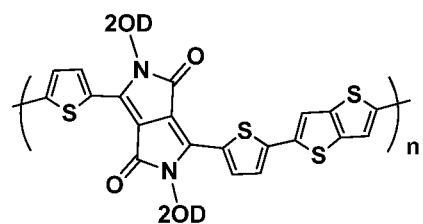

In one prior art, polymers with longer alkyl chains (e.g., 2-decyltetradecyl or referred to as 2DT in short, which is a branched alkyl chain with a formula of C10C14, shown in FIG. 4A)_exhibit higher performances than polymers with shorter alkyl chains (e.g., 2-octyldodecyl or referred to as 2OD in short, which is a branched alkyl chain with a formula of C8C12, shown in FIG. 4B). In a prior art example (*Adv. Mater.,* 2013, 25, 3182-3186, FIG. 4C), the polymer with 2DT alkyl chain exhibits a PCE of 6.9%, while the polymer with shorter 2OD alkyl chain (*Solar Energy Materials & Solar Cells,* 2011, 95, 1168-1173, FIG. 4D) exhibit a PCE of only 1.6%.

However, in this invention, the choice of branched alkyl has a dramatic but surprising effect on OPV performance that is completely opposite to the trend observed in prior art for 2DT (*Adv. Mater.,* 2013, 25, 3182-3186, FIG. 4C) and 2OD (*Solar Energy Materials & Solar Cells,* 2011, 95, 1168-1173, FIG. 4D) polymers. For the conjugated polymer in the present teaching, replacement of a 2DT branched alkyl chain with a 2OD branch alkyl chain surprising provided an increase of OPV efficiency from 7.6% to 10.8%. It was surprisingly found that conjugated polymers with alkyl chains that contain less than 23 carbon atoms (such as 2OD, C8C12 or 2DD C10C12) have dramatically higher performance than conjugated polymers with alkyl chains that contain 24 carbon atoms (such as 2DT, C10C14, alkyl chain).

In addition, the molecular weight of the conjugated polymer shown in above also has surprisingly large effects on the performance of OPV devices. It was found that the molecular weight of the 2OD-based polymers has a dramatic effect on its OPV performance. When the number average molecular weight of the conjugated polymer was increase from 17,000 to 47,000 gram/mole, the OPV efficiency was increased from 7.7% to 10.8%.

Figure 5:
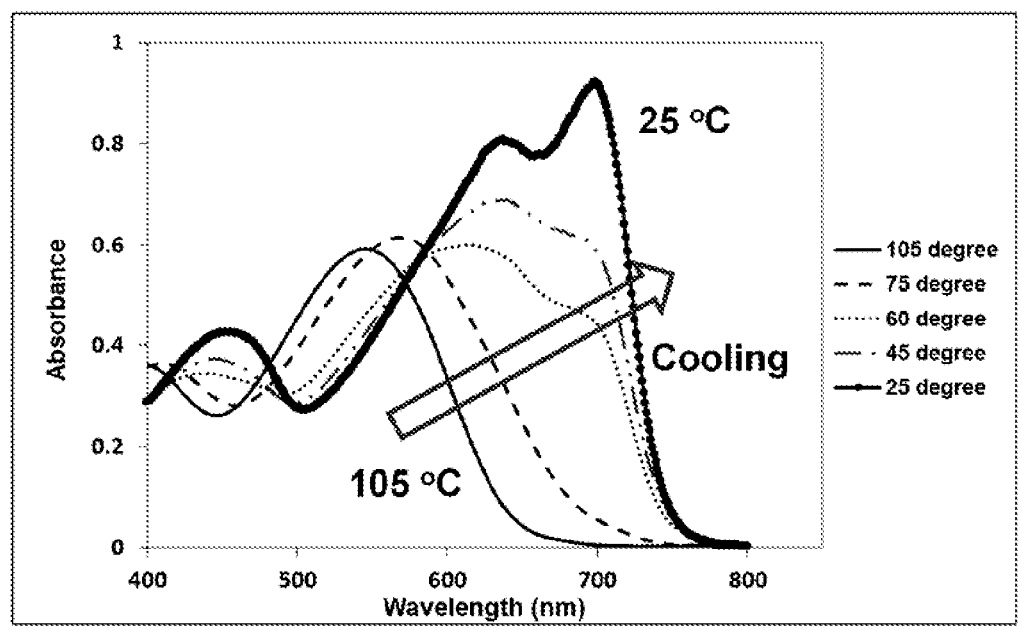
FIG. 5 shows the temperature dependent UV absorption properties of the polymers in the present invention.

A composition (or called polymer solution) comprises the above-mentioned conjugated polymer dissolved or dispersed in a liquid medium. It was found that the conjugated polymers show a dramatic red shift (>100 nm) in the peak of its optical absorption spectrum when the polymer solution is cooled from high temperatures (e.g., about 120° C.) to room temperature (FIG. 5). Surprisingly and beneficially, conjugated polymers based on such building blocks and with such optical properties were found to form an optimal polymer/fullerene morphology with a fullerene and to yield high-efficiency OPVs. The dramatic shift in UV absorption indicates excellent pi-pi stacking of the conjugated polymers and explains their superior charge transport ability.

In a second embodiment of the present invention, a conjugated polymer containing 10 or more repeating units of Formula (II) is provided:

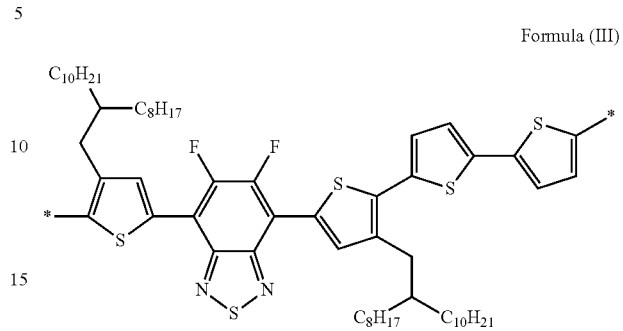

Formula (II)

wherein:
  R, at each occurrence, independently is selected from straight-chain, branched or cyclic alkyl with 2-40 C atoms; and
  Ar is selected from thiophene-based structure, or selenophene-based structure, or unsubstituted or substituted benzene-based structure, or combination of such groups; Ar does not contain any polycyclic group. In one example of this embodiment, Ar is preferred oligothiophene or oligo-selenophene (such as bithiophen).

In another example of this embodiment, the group Ar of the conjugated polymer, does not contain any alkyl substitution group, so as to obtain preferred polymer with higher molecular weight (for example, the number average molecular weight of the conjugated polymer is at least 30,000 gram/mole).

In still another example of this embodiment, the group R of the conjugated polymer, at each occurrence, independently is selected from branched alkyl groups with 15-25 carbon atoms, or with 17-23 carbon atoms, or more preferably 18-22 carbon atoms.

A composition (or called polymer solution) comprises the above-mentioned conjugated polymer dissolved or dispersed in a liquid medium. The composition exhibits a peak optical absorption spectrum red shift of at least 100 nm when the composition is cooled from about 120° C. to room temperature.

In a third embodiment of the present invention, a conjugated polymer containing 10 or more repeating units of Formula (III) is provided:

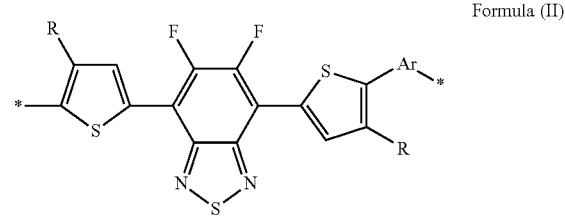

Formula (III)

wherein the number average molecular weight of the polymer is at least 30,000 gram/mole, or more preferably 40,000 gram/mole.

A composition (or called polymer solution) comprises the above-mentioned conjugated polymer dissolved or dispersed in a liquid medium. The composition exhibits a peak optical absorption spectrum red shift of at least 100 nm when the composition is cooled from about 120° C. to room temperature.

An organic photovoltaic device comprising a n-type semiconductor material adjacent to the above-mentioned conjugated polymer, and the power conversion efficiency is at least 8%, or more preferably 10%.

The following examples are provided to illustrate further and to facilitate the understanding of the present teachings and are not in any way intended to limit the invention.

Example 1—Synthesis of High-Performance Polymer 1

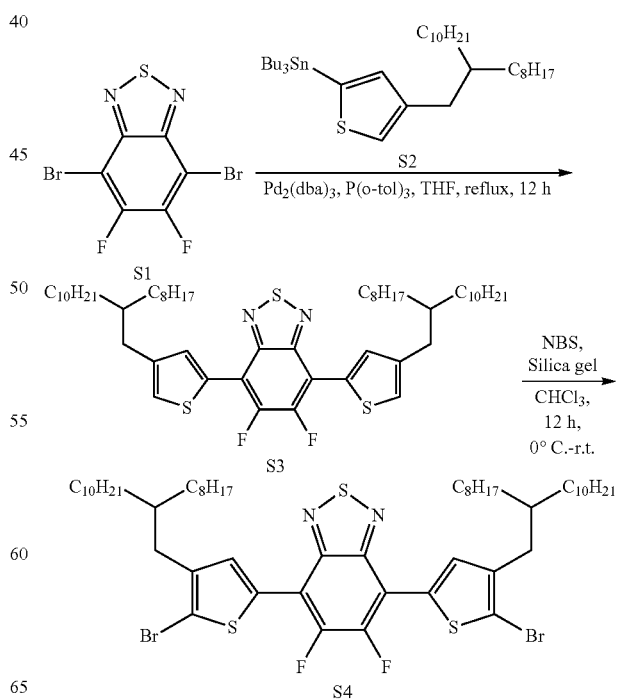

Step 1: Preparation of 5,6-Difluoro-4,7-bis(4-(2-octyldodecyl)-2-thienyl)-2,1,3-benzothiadiazole (S3)

A solution of 3-(2-octyldodecyl)thiophene (5.00 g, 13.7 mmol) in 50 mL THF was cooled to −78° C. under N2. Lithium diisopropylamide (2 M, 8.3 mL, 16.6 mmol) was added dropwise and the mixture was stirred at −78° C. for 1 h and then return to 0° C. and stirred for additional 1 h. Then the mixture was cooled to −78° C. and tri-n-butyltin chloride (6.50 g, 20 mmol) was added in one portion. The reaction mixture was return to r.t. and stirred overnight. A solution of KF in water was added and the organic phase was washed with water for three times, then dried with Na2SO4. The solvent was evaporated to get the crude product as yellow oil, which is directly used without further purification. A mixture of 2-(tri-n-butylstannyl)-4-(2-octyldodecyl) thiophene (1.96 g, 3 mmol), 4,7-dibromo-5,6-difluoro-2,1,3-benzothiadiazole (330 mg, 1 mmol), $Pd_2(dba)_3$ (11 mg, 0.02 mmol) and $P(o\text{-tol})_3$ (24 mg, 0.08 mmol) in 10 mL THF was refluxed overnight under N2. The reaction mixture was then cooled to r.t. and the solvent was evaporated. The residue was purified by flash column chromatography (eluent: n-hexane) to get the product as yellow solid (650 mg, 73%). $^1$H NMR (400 MHz, CDCl3) δ 8.11 (s, 2H), 7.19 (s, 2H), 2.66 (d, J=6.7 Hz, 4H), 1.77-1.62 (m, 2H), 1.42-1.14 (m, 64H), 0.97-0.84 (m, 12H). $^{13}$C NMR (100 MHz, CDCl3) δ 151.15, 150.95, 148.94, 148.57, 148.36, 142.36, 132.81, 130.99, 124.83, 111.76, 111.72, 111.67, 111.63, 38.97, 34.88, 33.34, 31.93, 30.05, 29.71, 29.67, 29.38, 26.66, 22.70, 14.12. HRMS (MALDI+) Calcd for $C_{54}H_{86}F_2N_2S_3$: 896.5921. Found: 896.5943.

Step 2: Preparation of 5,6-Difluoro-4,7-bis(5-bromo-4-(2-octyldodecyl)-2-thienyl)-2,1,3-benzothiadiazole (S4)

N-Bromosuccinimide (540 mg, 3.00 mmol) was added to a mixture of S3 (1.22 g, 1.36 mmol) and silica gel (20 mg) in 20 mL chloroform at 0° C. The reaction mixture was warmed to r.t. and stirred overnight. After washed with water, the organic phase was dried with Na2SO4 and the solvent was evaporated. The residue was purified with flash column chromatography (eluent: n-hexane) to get the product as orange solid (1.42 g, 99%). $^1$H NMR (400 MHz, CDCl3) δ 7.94 (s, 2H), 2.60 (d, J=7.1 Hz, 4H), 1.80-1.70 (m, 2H), 1.40-1.15 (m, 64H), 0.90-0.77 (m, 12H). $^{13}$C NMR (100 MHz, CDCl3) δ 150.95, 150.75, 148.36, 148.27, 148.16, 141.71, 132.27, 131.01, 115.14, 110.91, 110.82, 38.53, 34.09, 33.36, 31.95, 30.05, 29.74, 29.69, 29.68, 29.40, 26.56, 22.71, 14.13. HRMS (MALDI+) Calcd for $C_{54}H_{84}Br_2F_2N_2S_3$: 1052.4131. Found: 1052.4141.

Step 3: Polymer Synthesis

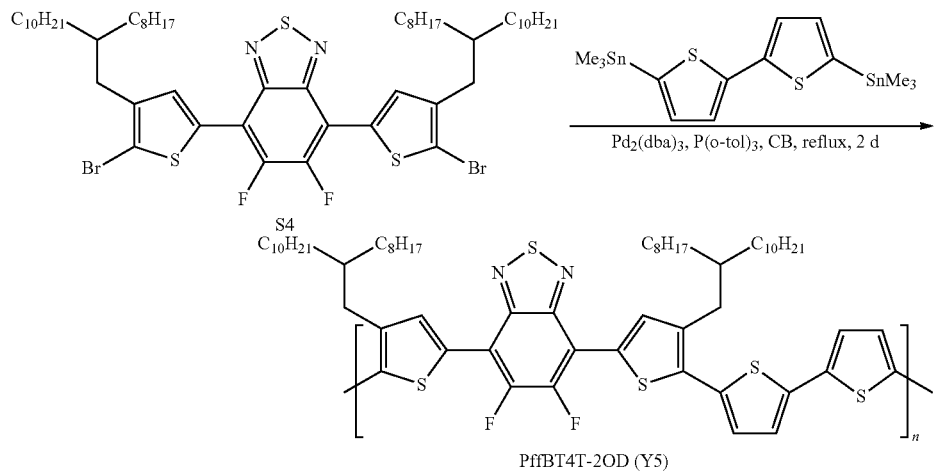

The PffBT4T-2OD can be synthesized by conventional reaction. To a mixture of monomer S4 (100 mg, 0.095 mmol), 5,5'-bis(trimethylstannyl)-2,2'-bithiophene (46.7 mg, 0.095 mmol), $Pd_2(dba)_3$ (1.1 mg, 0.002 mmol) and $P(o\text{-tol})_3$ (2.4 mg, 0.008 mmol) was added 1.6 mL of chlorobenzene in a glove box protected with $N_2$. The reaction mixture was then sealed and heated at 145° C. for 2 days. The mixture was cooled to r.t. and 10 mL toluene was added before precipitated with methanol. The solid was collected by filtration, and purified by Soxhlet extraction ($CH_2Cl_2$, $CHCl_3$, and chlorobenzene) and repetitive precipitation. The solvent was evaporated and the residue was dissolved in chlorobenzene and precipitated with methanol. The solid was collected by filtration and dried in vacuo to get the polymer as dark green solid (89 mg, 88%). $^1$H NMR (400 MHz, Toluene-d8, 359 K). δ 8.31 (br, 2H), 7.19 (br, 2H), 7.11 (br, 2H), 3.03 (br, 4H), 2.09 (br, 2H), 1.70-1.25 (m, 64H), 0.94 (br, 12H). Elem. Anal. Calcd for $C_{62}H_{88}F_2N_2S_5$: C, 70.27; H, 8.37; F, 3.59; N, 2.64; S, 15.13. Found: C, 70.33; H, 8.16; F, 3.70; N, 2.72; S, 14.91. GPC Number-averaged molecular weight (Mn): 39-47 kDa; weight-averaged molecular weight (Mw): 72-94 kDa.

Example 2—Synthesis of High-Performance Polymer 2

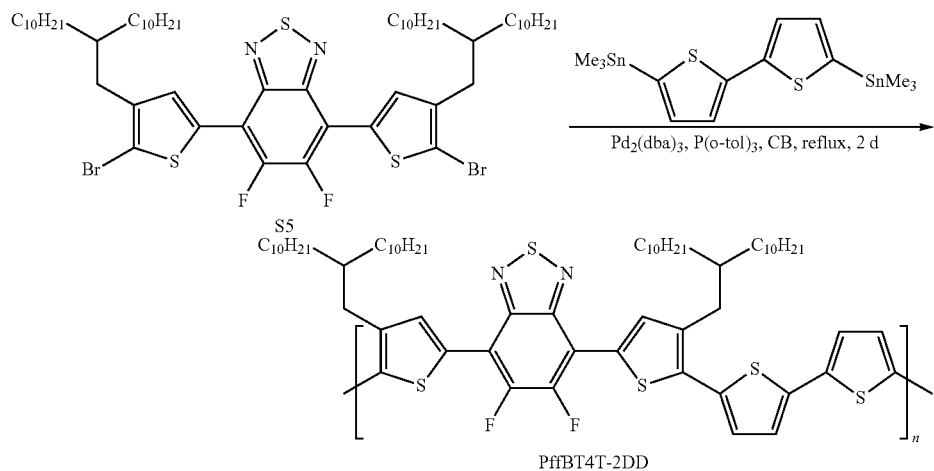

Polymer synthesis. PffBT4T-2DD (C10C12) can be synthesized by conventional reaction. To a mixture of monomer S5 (54.3 mg, 0.049 mmol), 5,5'-bis(trimethylstannyl)-2,2'-bithiophene (24.5 mg, 0.049 mmol), Pd$_2$(dba)$_3$ (1.0 mg, 0.002 mmol) and P(o-tol)$_3$ (2.0 mg, 0.007 mmol) was added 1.2 mL of chlorobenzene in a glove box protected with N$_2$. The reaction mixture was then sealed and heated at 145° C. for 2 days. The mixture was cooled to r.t. and 10 mL toluene was added before precipitated with methanol. The solid was collected by filtration, and purified by Soxhlet extraction (CH$_2$Cl$_2$, CHCl$_3$, and chlorobenzene) and repetitive precipitation. The solvent was evaporated and the residue was dissolved in chlorobenzene and precipitated with methanol. The solid was collected by filtration and dried in vacuo to get the polymer as dark green solid (37 mg, 68%). $^1$H NMR (400 MHz, Toluene-d8, 359 K). δ 8.31 (br, 2H), 7.19 (br, 2H), 7.11 (br, 2H), 3.03 (br, 4H), 2.09 (br, 2H), 1.70-1.25 (m, 68H), 0.94 (br, 12H). GPC Number-averaged molecular weight (Mn): 35 kDa; weight-averaged molecular weight (Mw): 61 kDa.

Example 3—Synthesis of High-Performance Polymer 3

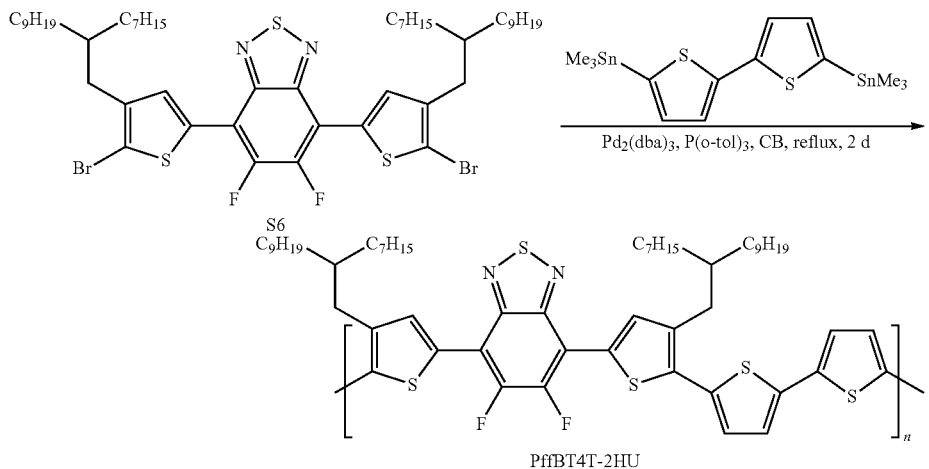

Polymer synthesis of PffBT4T-2HU (C7C11) can be synthesized by conventional reaction. To a mixture of monomer S5 (100 mg, 0.095 mmol), 5,5'-bis(trimethylstannyl)-2,2'-bithiophene (46.7 mg, 0.095 mmol), Pd$_2$(dba)$_3$ (1.1 mg, 0.002 mmol) and P(o-tol)$_3$ (2.4 mg, 0.008 mmol) was added 1.6 mL of chlorobenzene in a glove box protected with N$_2$. The reaction mixture was then sealed and heated at 145° C. for 2 days. The mixture was cooled to r.t. and 10 mL toluene was added before precipitated with methanol. The solid was collected by filtration, and purified by Soxhlet extraction (CH$_2$Cl$_2$, CHCl$_3$, and chlorobenzene) and repetitive precipitation. The solvent was evaporated and the residue was dissolved in chlorobenzene and precipitated with methanol. The solid was collected by filtration and dried in vacuo to get the polymer as dark green solid (81 mg, 85%). $^1$H NMR (400 MHz, Toluene-d8, 359 K). δ 8.31 (br, 2H), 7.19 (br, 2H), 7.11 (br, 2H), 3.03 (br, 4H), 2.09 (br, 2H), 1.70-1.25 (m, 60H), 0.94 (br, 12H). GPC Number-averaged molecular weight (Mn): 37 kDa; weight-averaged molecular weight (Mw): 69 kDa.

Example 4—Comparative Example #1, Synthesis of Low Molecular Weight PffBT4T-2OD

The PffBT4T-2OD can be synthesized by conventional reaction. To a mixture of monomer S4 (100 mg, 0.095 mmol), 5,5'-bis(trimethylstannyl)-2,2'-bithiophene (46.7 mg, 0.095 mmol), Pd$_2$(dba)$_3$ (1.1 mg, 0.002 mmol) and P(o-tol)$_3$ (2.4 mg, 0.008 mmol) was added 8 mL of chlorobenzene in a glove box protected with N$_2$. The reaction mixture was then sealed and heated at 100° C. for 1 days. The mixture was cooled to r.t. and 10 mL toluene was added before precipitated with methanol. The solid was collected by filtration, and purified by Soxhlet extraction (CH$_2$Cl$_2$, CHCl$_3$, and chlorobenzene) and repetitive precipitation. The solvent was evaporated and the residue was dissolved in chlorobenzene and precipitated with methanol. The solid was collected by filtration and dried in vacuo to get the polymer as dark green solid (60 mg). $^1$H NMR (400 MHz, Toluene-d8, 359 K). δ 8.31 (br, 2H), 7.19 (br, 2H), 7.11 (br, 2H), 3.03 (br, 4H), 2.09 (br, 2H), 1.70-1.25 (m, 64H), 0.94 (br, 12H). GPC Number-averaged molecular weight (Mn): 17 kDa; weight-averaged molecular weight (Mw): 30 kDa.

Example 5—Comparative Example #2, PffBT4T-2DT, Synthesis of Polymer with Longer Alkyl Chains (2DT) than PffBT4T-2OD

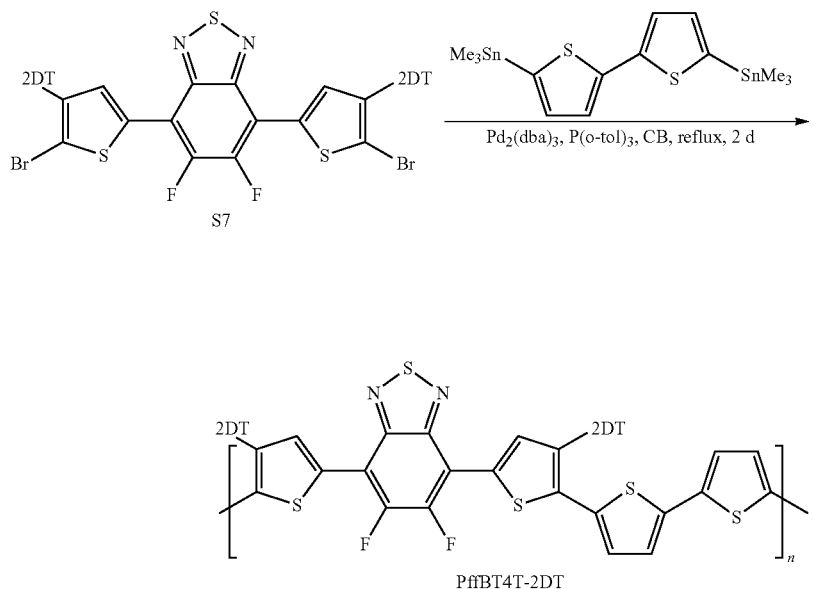

The PffBT4T-2DT can be synthesized by microwave reaction. To a mixture of monomer S5 (105 mg, 0.095 mmol), 5,5'-bis(trimethylstannyl)-2,2'-bithiophene (46.7 mg, 0.095 mmol), Pd$_2$(dba)$_3$ (1.1 mg, 0.002 mmol) and P(o-tol)$_3$ (2.4 mg, 0.008 mmol) was added 1.6 mL of chlorobenzene in a glove box protected with N$_2$. The reaction mixture was then sealed and at 160° C. for 30 min for microwave reaction. The mixture was cooled to r.t. and 10 mL toluene was added before precipitated with methanol. The solid was collected by filtration, and purified by Soxhlet extraction (CH$_2$Cl$_2$, CHCl$_3$, and chlorobenzene) and repetitive precipitation. The solvent was evaporated and the residue was dissolved in chlorobenzene and precipitated with methanol. The solid was collected by filtration and dried in vacuo to get the polymer as dark green solid (77 mg). $^1$H NMR (400 MHz, Toluene-d8, 359 K). δ 8.31 (br, 2H), 7.19 (br, 2H), 7.11 (br, 2H), 3.03 (br, 4H), 2.09 (br, 2H), 1.70-1.25 (m, 72H), 0.94 (br, 12H). GPC Number-averaged molecular weight (Mn): 35 kDa; weight-averaged molecular weight (Mw): 78 kDa.

Example 6—Comparative Example #3, PffBT4T-2HD, Synthesis of Polymer with Shorter Alkyl Chains (2HD) than PffBT4T-2OD

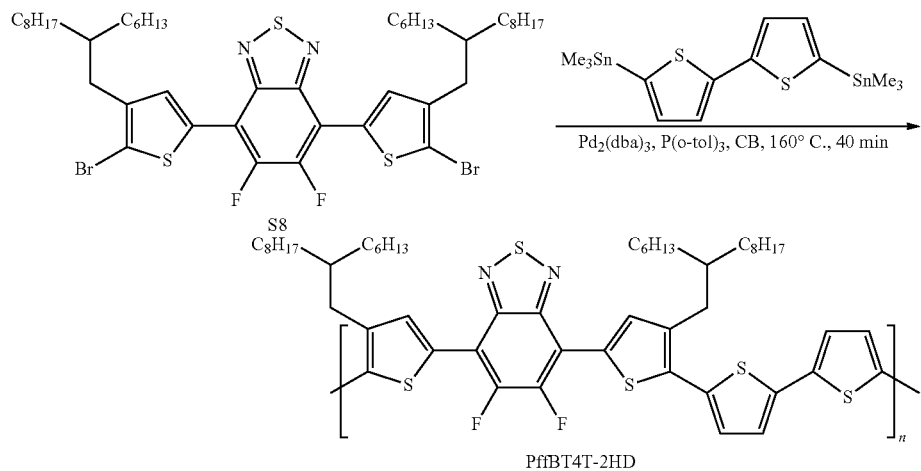

PffBT4T-2HD. To a mixture of monomer S8 (35.0 mg, 0.0371 mmol), 5,5'-bis(trimethylstannyl)-2,2'-bithiophene (18.6 mg, 0.0379 mmol), Pd$_2$(dba)$_3$ (0.6 mg, 0.0007 mmol) and P(o-tol)$_3$ (1.2 mg, 0.004 mmol) in a microwave vial equipped with a stirring bar was added 0.15 mL of chlorobenzene in a glove box protected with N$_2$. The reaction mixture was then sealed and heated to 160° C. for 40 min using a microwave reactor. The mixture was cooled to r.t. and 5 mL of chlorobenzene was added before precipitated with methanol. The solid was collected by filtration, and loaded into an extraction thimble and washed with CHCl$_3$. The polymer was finally collected from chlorobenzene. The chlorobenzene solution was then concentrated by evaporation, precipitated into methanol. The solid was collected by filtration and dried in vacuo to get the polymer as dark green solid (6.7 mg, 19%).

$^1$H NMR (400 MHz, C2 D2Cl4, 408 K). δ 8.21 (s, 2H), 7.27 (s, 4H), 2.95 (d, J=6.9 Hz, 4H), 1.94 (br, 2H), 1.59-1.27 (m, 48H), 0.99-0.90 (m, 12H).

GPC Mn=13.9 kDa; Mw=25.8 kDa; PDI=1.85.

Example 7—Comparative Example #4, Low-Performance Polymers with Alkyl Groups on the Ar Unit

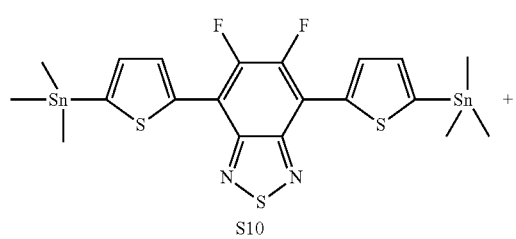

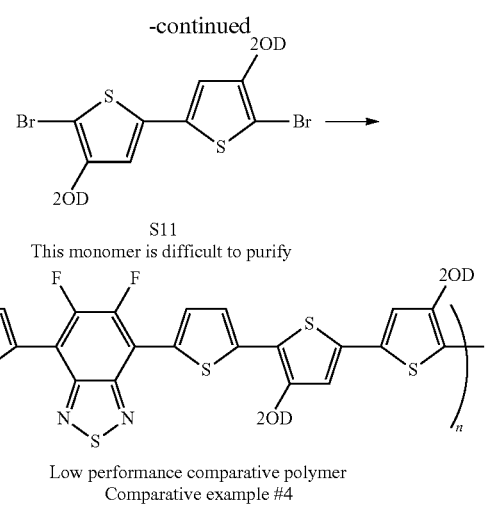

Polymer synthesis comparative example #4, this polymer was synthesized by conventional reaction. To a mixture of monomer S10 (18.6 mg), S11 (24.9 mg), Pd$_2$(dba)$_3$ (0.5 mg, 0.001 mmol) and P(o-tol)$_3$ (1.2 mg, 0.004 mmol) was added 1.0 mL of chlorobenzene in a glove box protected with N2. The reaction mixture was then sealed and heated at 145° C. for 2 days. The mixture was cooled to r.t. and 10 mL toluene was added before precipitated with methanol. The solid was collected by filtration, and purified by Soxhlet extraction (CH$_2$Cl$_2$, CHCl$_3$, and chlorobenzene) and repetitive precipitation. The solvent was evaporated and the residue was dissolved in chlorobenzene and precipitated with methanol. The solid was collected by filtration and dried in vacuo to get the polymer as dark green solid (20 mg, 67%). GPC Number-averaged molecular weight (Mn): 8 kDa; weight-averaged molecular weight (Mw): 13 kDa.

Example 8—Synthesis of Monomer/Polymer

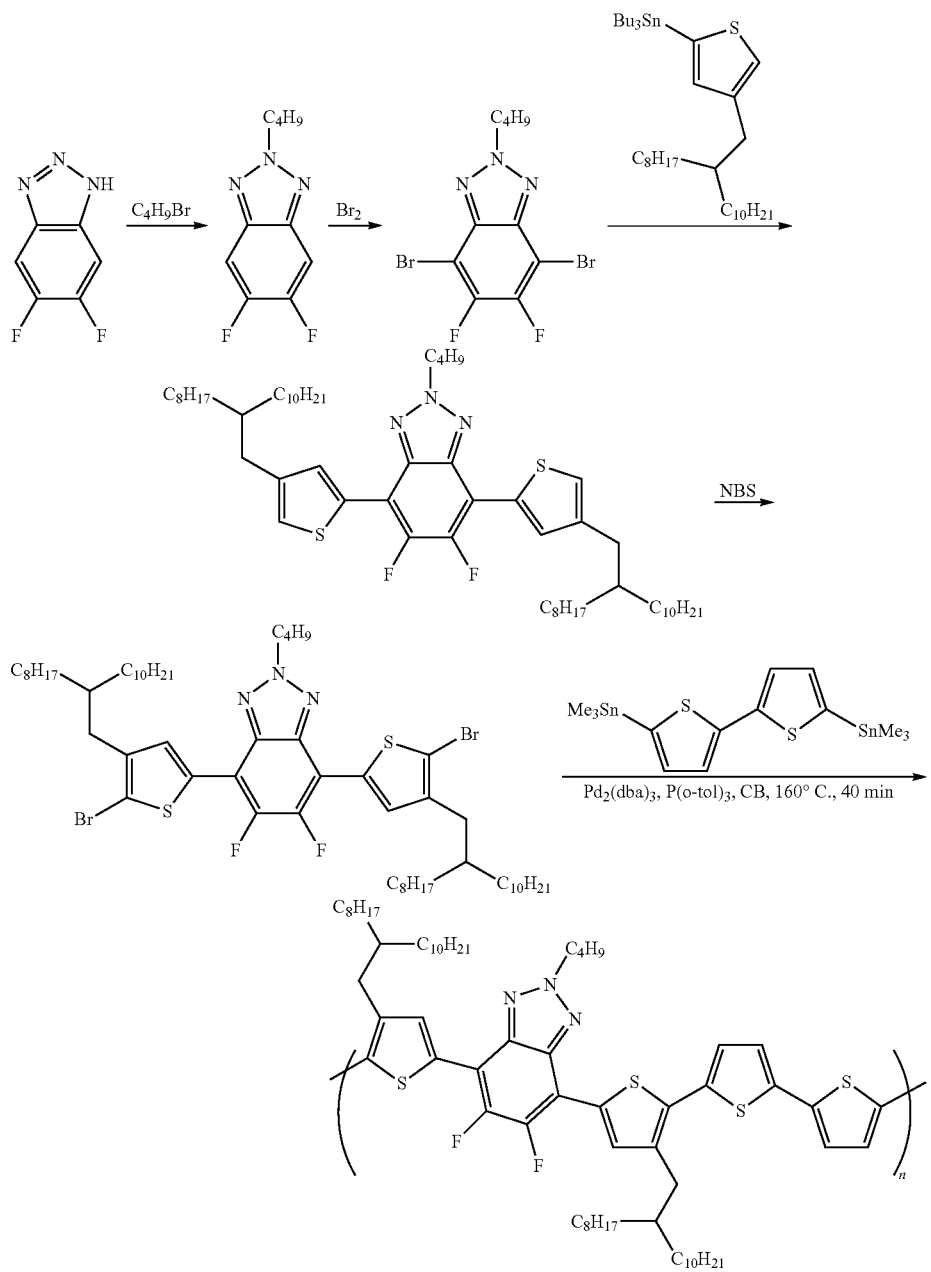

Step 1: Preparation of
2-butyl-5,6-Difluoro-1,2,3-benzotriazole

A solution of 5,6-difluoro-1,2,3-benzotriazole in 50 mL THF was added KOH and stir at r.t. for 15 min. Then n-butyl bromide was added. The mixure was allowed to stir at reflux temperature for 12 h. After returning to r.t., the solution was washed with water and extracted with dichloromethane. The organic layer was separated and dried over anhydrous sodium sulphate. The solvent was removed and the crude product was purified by column chromatography (eluent: n-hexane/dichloromethane=10/1) to get white solid.

Step 2: Preparation of 4,7-dibromo-2-butyl-5,6-Difluoro-1,2,3-benzotriazole 2-butyl-5,6-Difluoro-1,2,3-benzotriazole was dissolved in 50 mL trifluoroacetic acid and was cooled to 0° C. Bromide was added dropwise. The mixture was stirred r.t. for 12 h. Then the solution was extracted with dichloromethane and washed with water for three times. The organic layer was separated and dried over anhydrous sodium sulphate. The solvent was removed and the crude product was purified by column chromatography (eluent: n-hexane/dichloromethane=12/1) to get white solid.

Step 3: Preparation of 2-butyl-5,6-difluoro-4,7-bis(4-(2-octyldodecyl)thiophen-2-yl)-1,2,3-benzotriazole A mixture of 2-(tri-n-butylstannyl)-4-(2-octyldodecyl)thiophene (1.96 g, mmol), 4,7-dibromo-2-butyl-5,6-Difluoro-1,2,3-benzotriazole (330 mg, 1 mmol) and Pd (PPh₃)₄ in 10 mL toluene was refluxed overnight under $N_2$. The reaction mixture was then cooled to r.t. and the solvent was evaporated. The residue was purified by column chromatography (eluent: n-hexane/dichloromethane=5/1) to get the product as red solid (650 mg, 73%).

Step 4: Preparation of 2-butyl-5,6-difluoro-4,7-bis(5-bromo-4-(2-octyldodecyl)thiophen-2-yl)-1,2,3-benzotriazole 2-butyl-5,6-difluoro-4,7-bis(4-(2-octyldodecyl)thiophen-2-yl)-1,2,3-benzotriazole was dissolved in 10 mL chloroform and cooled to 0° C. NBS was added in portions. The solution was stirred at r.t. for 3 h. Then the solution was extracted with chloroform and washed with water for three times. The organic layer was separated and dried over anhydrous sodium sulphate. The solvent was removed and the crude product was purified by column chromatography (eluent: n-hexane/dichloromethane=6/1) to get red solid.

Example 9—Synthesis of Monomer/Polymer

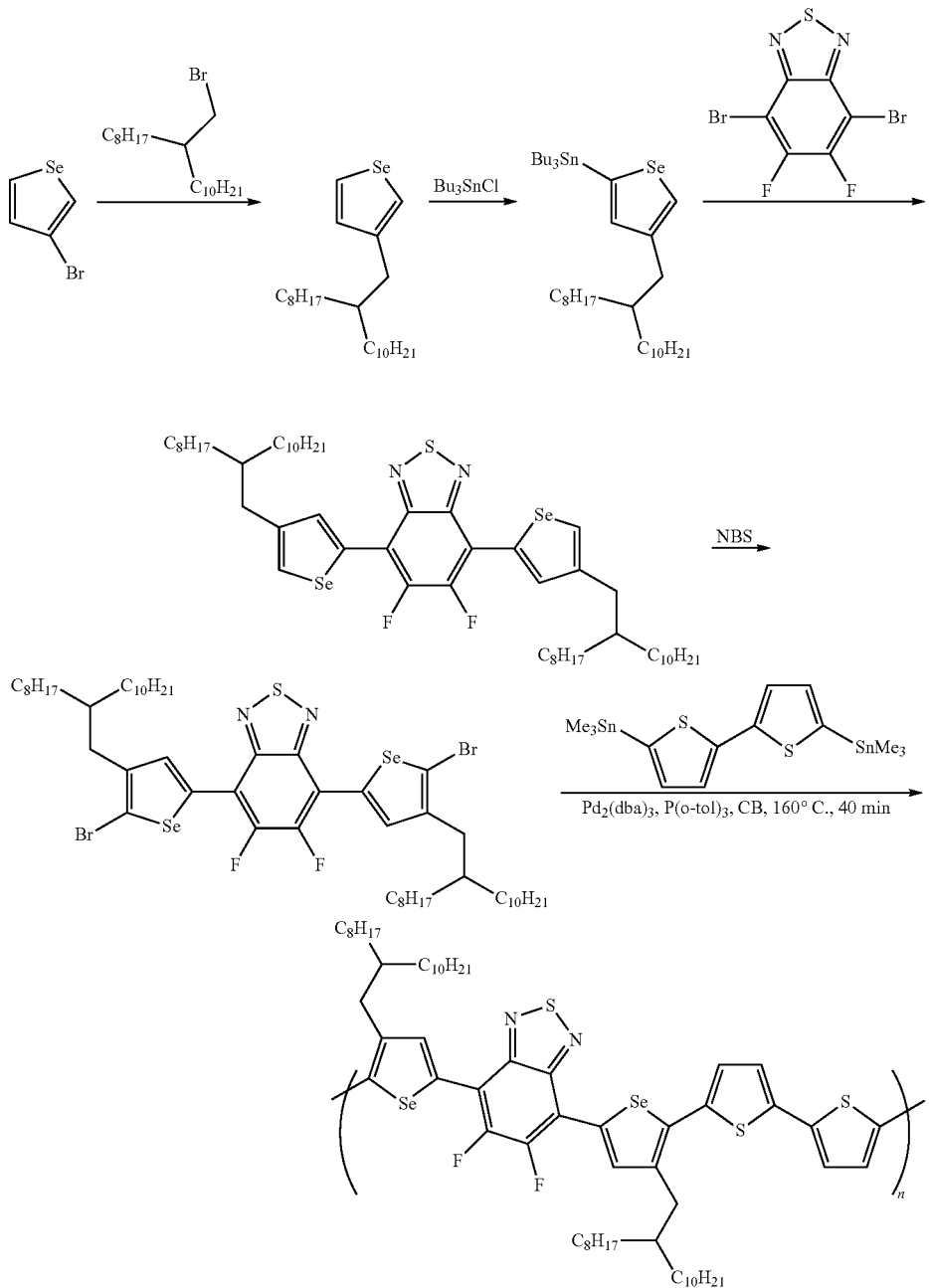

Step 1: Preparation of 3-(2-octyldodecyl)selenophene

A 3-bromoselenophene and Ni(dppp)Cl$_2$ was dissolved in diethyl ether under nitrogen and cooled to 0° C. 9-(bromomethyl)nonadecane was added dropwise. The mixture was stirred r.t. for 24 h. Then the reaction mixture was washed with water and extracted with diethyl ether. The organic layer was separated and dried over anhydrous sodium sulphate. The solvent was removed and the crude product was purified by column chromatography (eluent: n-hexane) to get product as colorless oil.

Step 2: 2-(tri-n-butylstannyl)-4-(2-octyldodecyl)selenophene

A solution of 3-(2-octyldodecyl)selenophene (5.00 g, 13.7 mmol) in 50 mL THF was cooled to −78° C. under N2. Lithium diisopropylamide (2 M, 8.3 mL, 16.6 mmol) was added dropwise and the mixture was stirred at −78° C. for 1 h and then return to 0° C. and stirred for additional 1 h. Then the mixture was cooled to −78° C. and tri-n-butyltin chloride (6.50 g, 20 mmol) was added in one portion. The reaction mixture was return to r.t. and stirred overnight. A solution of KF in water was added and the organic phase was washed with water for three times, then dried with Na$_2$SO$_4$. The solvent was evaporated to get the crude product as yellow oil, which is directly used without further purification.

Step 3: Preparation of 5,6-difluoro-4,7-bis(4-(2-octyldodecyl)selenophen-2-yl)-2,1,3-benzothiadiazole A mixture of 2-(tri-n-butylstannyl)-4-(2-octyldodecyl)selenophene (1.96 g, 3 mmol), 4,7-dibromo-2,1,3-benzothiadiazole (330 mg, 1 mmol) and Pd (PPh$_3$)$_4$ in 10 mL toluene was refluxed overnight under N$_2$. The reaction mixture was then cooled to r.t. and the solvent was evaporated. The residue was purified by column chromatography (eluent: n-hexane/dichloromethane=5/1) to get the product as red solid (650 mg, 73%).

Step 4: Preparation of 5,6-difluoro-4,7-bis(5-bromo-4-(2-octyldodecyl)selenophen-2-yl)-2,1,3-benzothiadiazole 5,6-difluoro-4,7-bis(4-(2-octyldodecyl)selenophen-2-yl)-2,1,3-benzothiadiazole was dissolved in 10 mL chloroform and cooled to 0° C. NBS was added in portions. The solution was stirred at r.t. for 3 h. Then the solution was extracted with chloroform and washed with water for three times. The organic layer was separated and dried over anhydrous sodium sulphate. The solvent was removed and the crude product was purified by column chromatography (eluent: n-hexane/dichloromethane=6/1) to get red solid.

Example 10—Synthesis of Fullerenes-PC$_{71}$BM

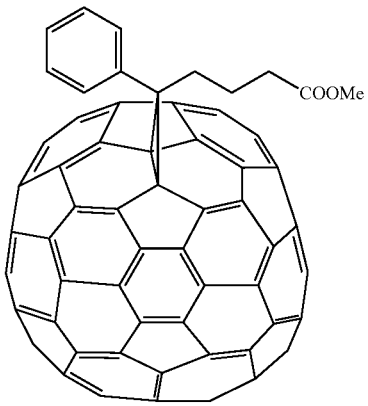 [SMILES: COC(=O)CCCC1(c2ccccc2)C23c4c5ccc6c7cc8c9c%10c%11c%12c(cc%13c%14c%15c(cc%16c%17ccc-5c2c%17c2c5c%17c%18c(c(c46)c7c9c%18c%11c(c%14%12)c%17c%15c%162)C513)C%13)CC%10C8]

The tosyl hydrazone of methyl benzoylbutyrate (415.6 mg; 1.11 mmol) and sodium methoxide (59.4 mg; 1.1 mmol, 0.99 eq.) were suspended in dry pyridine (15 mL) under an atmosphere of dry nitrogen and the mixture was stirred at room temperature for ~25 min. To the resulting solution was added a solution of C$_{70}$ (840 mg, 1 mmol; 99.5%, MTR) in HPLC grade ODCB (75 mL). The reaction mixture was heated to 75° C. in the dark under an atmosphere of N2 until the formation of the [5,6]-adducts ceased (monitored by HPLC). The reaction mixture was allowed to cool to ambient temperature. Subsequently, the reaction mixture was irradiated with a 400 W sodium lamp until complete isomerization of the [5,6] isomers to the corresponding [6,6] isomers was obtained (as monitored by HPLC). The volatile components were evaporated in vacuo. The crude product was purified using column chromatography (Silicagel/ODCB). After elution of recovered [70]fullerene, a brown band of crude[70]PCBM isomers was eluted. The solvent was removed in vacuo and the remaining solid was transferred to a centrifugal bottle using a minimal amount of toluene and subsequently precipitated with MeOH. The residue was washed with MeOH (2×) and dried in vacuo at ~50° C. This resulted in 612 mg [70]PCBM (59%). $^1$H-NMR: (CS2/D2O): δ (ppm)=7.1-8.0 (m, phenyl; 5H), 3.48, 3.65 (major isomer), 3.72 (s, OCH$_3$; 3 H), 2.4-2.6 (m, PhCCH$_2$ and CH$_2$CO$_2$; 4 H), 2.1-2.3 (m, CH$_2$CH$_2$CO$_2$, ~2H), and 1.65-1.9 (m, CH$_2$CH$_2$CO$_2$; minor isomers). $^{13}$C NMR: (CS$_2$/D$_2$O): δ (ppm)=171 (C=O), 128-156 (70 resonances; C$_{70}$ and Ph), 69.0, 71.5 (C$_{70}$ sp3), 51.0, 51.1 (OCH$_3$ and PhCCH$_2$), 34.0, 33.5 (PhCCH$_2$ and CH$_2$CO$_2$), 22.0 (CH$_2$CH$_2$CO$_2$). IR (DRIFT): 2942(s), 1738(s), 1429(s), 795, 752, 698, 674, 644, 578, 534, and 459 cm$^{-1}$.

Ms(APCI): 1030.2 (calc. For C82H14O2: 1031.01).

Example 11—Organic Photovoltaic (OPV) Device Fabrication

Figure 6:
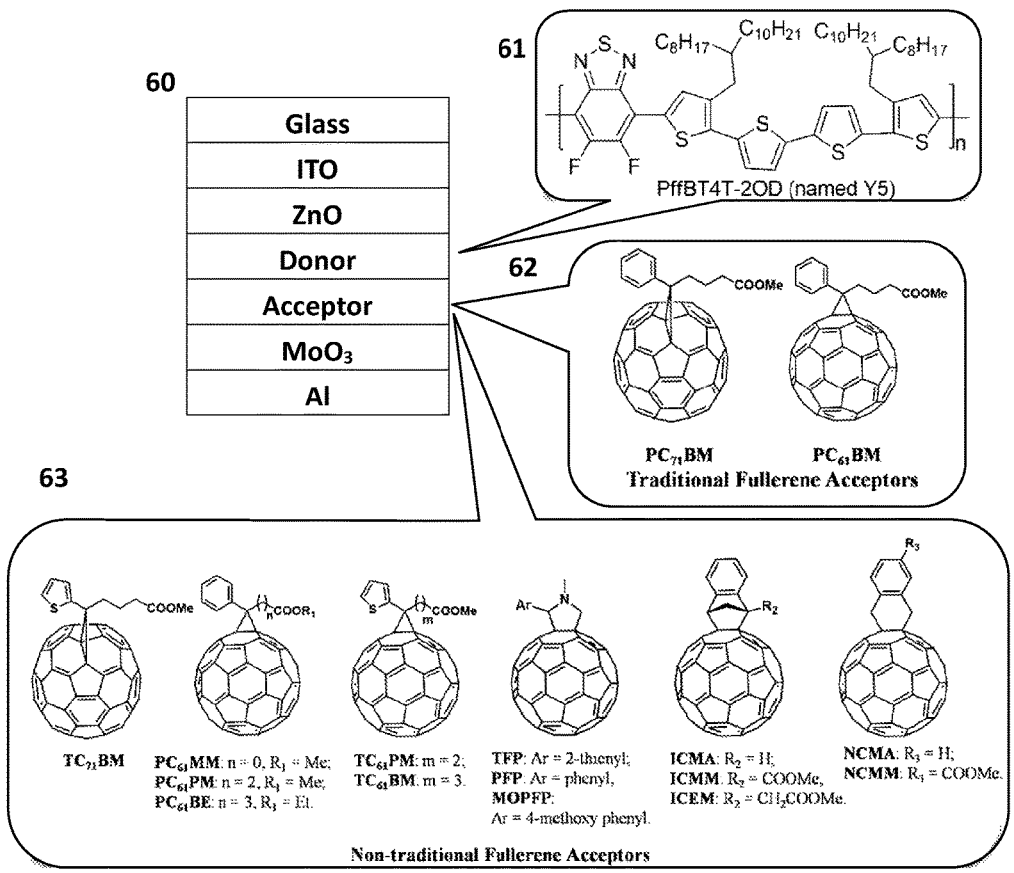
FIG. 6 is an illustration representing a bulk-heterojunction (BHJ) organic photovoltaic device (also known as a solar cell) structure, which can incorporate polymer and fullerene as its photoactive layer (respectively as donor and acceptor materials).
Figures 7A, 7B, 7C:
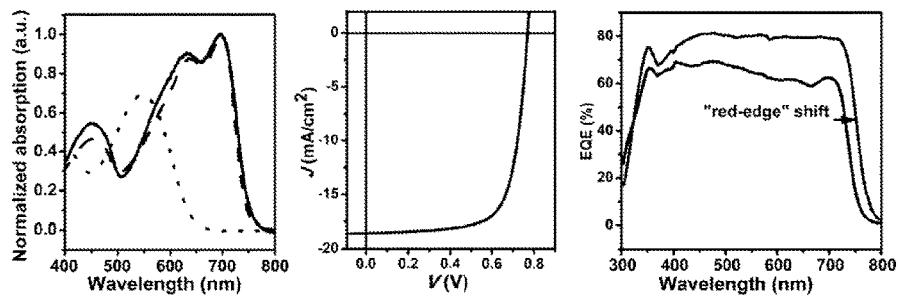
FIG. 7A shows the UV-Vis spectra of a polymer of the present teaching in thin film (solid line) and as a solution in DCB at 120° C. (dotted line) and at room temperature (dashed line)
FIG. 7B shows the J-V curves of representative thin and thick film PSC devices based upon a bulk heterojunction photoactive layer including a polymer of the present teaching as the donor material and fullerene as the acceptor material.
FIG. 7C shows the EQE spectrum of representative thin and thick film PSC devices based upon a bulk heterojunction photoactive layer including a polymer of the present teaching as the donor material and fullerene as the acceptor material.

Device structure 60 is shown in FIG. 6. An example of polymer in the present teaching is shown as 61. Many known fullerene compounds used in the present teaching are shown as 62 and 63. Pre-patterned ITO-coated glass with a sheet resistance of ~15 Ω/square was used as the substrate. It was cleaned by sequential sonication in soap DI water, DI water, acetone, and isopropanol. After UV/ozone treatment for 60 min, a ZnO electron transport layer was prepared by spin-coating at 5000 rpm from a ZnO precursor solution (diethyl zinc). Active layer solutions were prepared in CB/DCB or CB/DCB/DIO with various ratios (polymer concentration: 7-12 mg/mL). To completely dissolve the polymer, the active layer solution was stirred on hotplate at 100-120° C. for at least 3 hours. Active layers were spin-coated from warm solutions in a $N_2$ glovebox at 600-850 rpm to obtain thicknesses of ~250-350 nm. The polymer/fullerene films were then annealed at 80° C. for 5 min before being transferred to the vacuum chamber of a thermal evaporator inside the same glovebox. At a vacuum level of 3×10-6 Torr, a thin layer (20 nm) of $MoO_3$ or $V_2O_5$ was deposited as the anode interlayer, followed by deposition of 100 nm of Al as the top electrode. All cells were encapsulated using epoxy inside the glovebox. Device J-V characteristics was measured under AM1.5G (100 mW/cm$^2$) using a Newport solar simulator. The light intensity was calibrated using a standard Si diode (with KG5 filter, purchased from PV Measurement) to bring spectral mismatch to unity. J-V characteristics were recorded using a Keithley 236 source meter unit. Typical cells have a device area of about 5.9 mm$^2$, which is defined by a metal mask with an aperture aligned with the device area. EQEs were characterized using a Newport EQE system equipped with a standard Si diode. Monochromatic light was generated from a Newport 300 W lamp source. The J-V and EQE plots of OPV devices in the present teaching are shown in FIG. 7B, 7C. The Voc, Jsc, FF and PCE of OPV devices in the present teaching are summarized in the following two tables.

TABLE 1

High-performance polymers in present teaching (efficiency 9.3-10.8%)
(All polymers have high molecular weight, Mn > 30 kDa.)

| Active layer | $V_{OC}$ [V] | $J_{SC}$ [mA cm$^{-2}$] | FF | PCE [%] |
|---|---|---|---|---|
| PffBT4T-2OD*: T$C_{71}$BM | 0.77 | 18.8 | 0.75 | 10.8 |
| *Note 2OD has 20 carbons atoms | | | | |
| PffBT4T-2OD: P$C_{71}$BM | 0.77 | 18.6 | 0.73 | 10.4 |
| PffBT4T-2OD: P$C_{61}$PM | 0.78 | 17.5 | 0.75 | 10.2 |
| PffBT4T-2OD: ICMA | 0.78 | 16.4 | 0.77 | 9.8 |
| PffBT4T-2OD: T$C_{61}$PM | 0.75 | 17.4 | 0.74 | 9.7 |
| PffBT4T-2OD: P$C_{61}$BM | 0.75 | 17.3 | 0.73 | 9.6 |
| PffBT4T-2DD* P$C_{71}$BM | 0.75 | 17.6 | 0.71 | 9.4 |
| *Note 2DD has 22 carbons atoms | | | | |
| PffBT4T-2HU*: P$C_{71}$BM | 0.76 | 17.5 | 0.70 | 9.3 |
| *Note 2DD has 18 carbons atoms | | | | |

TABLE 2

Low-performance comparative polymer examples,
the fullerene used is P$C_{71}$BM

| Active layer | $V_{OC}$ [V] | $J_{SC}$ [mA cm$^{-2}$] | FF | PCE [%] |
|---|---|---|---|---|
| Comparative example #1, PffBT4T-2OD* | 0.72 | 16.7 | 0.63 | 7.7% |
| *Low molecular weight polymer, Mn ~17 kDa | | | | |
| Comparative example #2, PffBT4T-2DT* | 0.78 | 13.9 | 0.70 | 7.6% |
| *Note 2DT has 24 carbon atoms, which is too long | | | | |
| Comparative example #3, PffBT4T-2HD* | 0.73 | 15.0 | 0.62 | 6.8% |
| *Note 2HD has 16 carbon atoms, which is too short | | | | |

TABLE 2-continued

Low-performance comparative polymer examples,
the fullerene used is P$C_{71}$BM

| Active layer | $V_{OC}$ [V] | $J_{SC}$ [mA cm$^{-2}$] | FF | PCE [%] |
|---|---|---|---|---|
| Comparative example #4, *This polymer contain alkyl groups on the Ar unit | 0.74 | 16.1 | 0.52 | 6.3% |

The above embodiments are only used to illustrate the principles of the present invention, and they should not be construed as to limit the present invention in any way. The above embodiments can be modified by those with ordinary skill in the art without departing from the scope of the present invention as defined in the following appended claims.

What is claimed is:

1. A conjugated polymer containing 10 or more repeating units of Formula (I):

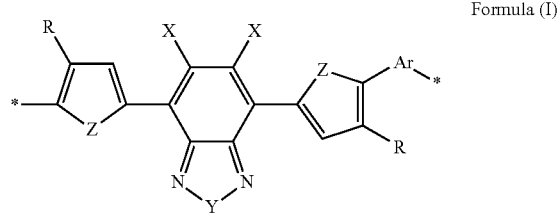

Formula (I)

wherein:
X, at each occurrence, independently is selected from F and Cl;
Y is selected from a group consisting of S and N—R1, wherein R1 is selected from a group consisting of C1-20 straight-chain and branched alkyl groups;
Z, at each occurrence, independently is selected from a group consisting of S and Se;
R, at each occurrence, independently is selected from a group consisting of straight-chain, branched and cyclic alkyl with 2-40 C atoms, in which one of more non-adjacent C atoms are optionally replaced by —O—, —S—, —C(O)—, —C(O-)-O—, —O—C(O)—, —O—C(O)—O—, —CR0=CR00- or —C≡C— and in which one or more H atoms are optionally replaced by F, Cl, Br, I or CN, or denote aryl, heteroaryl, aryloxy, heteroaryloxy, arylcarbonyl, heteroarylcarbonyl, arylcarbonyloxy, heteroarylcarbonyloxy, aryloxycarbonyl or heteroaryloxycarbonyl having 4 to 30 ring atoms that is unsubstituted or substituted by one or more non-aromatic groups;
and
Ar is selected from a group consisting of unsubstituted or substituted arylene, unsubstituted or substituted heteroarylene, and combination of such groups; wherein Ar does not contain any polycyclic group.

2. The conjugated polymer of claim 1, wherein Ar does not contain any alkyl substitution group.

3. The conjugated polymer of claim 1, wherein Ar is selected from:

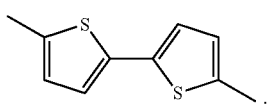

4. The conjugated polymer of claim 1, wherein:
R, at each occurrence, independently is selected from branched alkyl groups with 17-23 carbon atoms.

5. The conjugated polymer of claim 1, wherein the number average molecular weight of the conjugated polymer is at least 30,000 gram/mole.

6. A composition comprising the conjugated polymer of claim 1 dissolved or dispersed in a liquid medium.

7. The composition of claim 6, wherein the composition exhibits a peak optical absorption spectrum red shift of at least 100 nm when the composition is cooled from about 120° C. to room temperature.

8. An optical, electronic, or optoelectronic device comprising the conjugated polymer of claim 1.

9. The device of claim 8, wherein the device is selected from an organic field-effect transistor, an organic light-emitting transistor, and an organic photovoltaic device.

10. A conjugated polymer containing 10 or more repeating units of Formula (II):

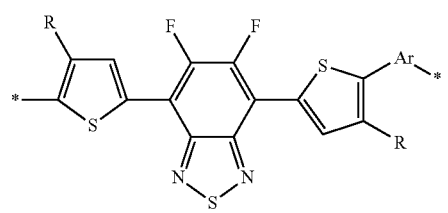

Formula (II)

wherein:
R, at each occurrence, independently is selected from straight-chain, branched or cyclic alkyl with 2-40 C atoms; and
Ar is selected from thiophene-based structure, or selenophene-based structure, or unsubstituted or substituted benzene-based structure, or combination of such groups; Ar does not contain any polycyclic group.

11. The conjugated polymer of claim 10, wherein Ar does not contain any alkyl substitution group.

12. The conjugated polymer of claim 10, wherein Ar is

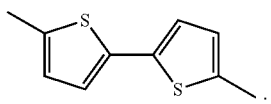

13. The conjugated polymer of claim 10, wherein:
R, at each occurrence, independently is selected from branched alkyl groups with 17-23 carbon atoms.

14. The conjugated polymer of claim 10, wherein the number average molecular weight of the conjugated polymer is at least 30,000 gram/mole.

15. A composition comprising the conjugated polymer of claim 10 dissolved or dispersed in a liquid medium.

16. The composition of claim 15, wherein the composition exhibits a peak optical absorption spectrum red shift of at least 100 nm when the composition is cooled from about 120° C. to room temperature.

17. The device of claim 8, wherein the device is selected from a group consisting of an organic field-effect transistor, an organic light-emitting transistor, and an organic photovoltaic device.

18. A conjugated polymer containing 10 or more repeating units of Formula (III):

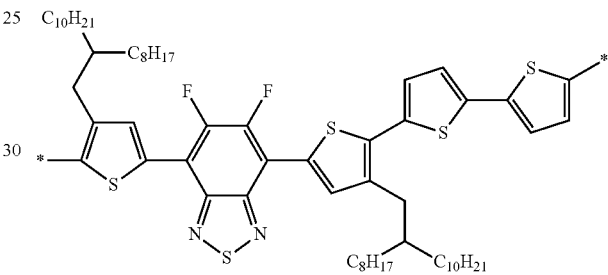

Formula (III)

wherein the number average molecular weight of the conjugated polymer is at least 30,000 gram/mole.

19. An optical, electronic, or optoelectronic device comprising the conjugated polymer of claim 18.

20. The device of claim 19, wherein the device is selected from an organic field-effect transistor, an organic light-emitting transistor, and an organic photovoltaic device.

21. A composition comprising the conjugated polymer of claim 18 dissolved or dispersed in a liquid medium.

22. The composition of claim 21, wherein the composition exhibits a peak optical absorption spectrum red shift of at least 100 nm when the composition is cooled from about 120° C. to room temperature.

23. An organic photovoltaic device comprising a n-type semiconductor material adjacent to the conjugated polymer of claim 18, and the power conversion efficiency is at least 8%.

* * * * *